(12) United States Patent
Dahan (10) Patent No.: US 8,381,582 B2
(45) Date of Patent: Feb. 26, 2013

(54) METHOD AND SYSTEM FOR MONITORING SOIL PROPERTIES

(75) Inventor: Ofer Dahan, Ben-Gurion (IL)

(73) Assignee: Ben-Gurion University of the Negev Research and Development Authority, Beer-Sheva (IL)

( * ) Notice: Subject to any disclaimer, the term of this patent is extended or adjusted under 35 U.S.C. 154(b) by 578 days.

(21) Appl. No.: 12/222,069

(22) Filed: Jul. 31, 2008

(65) Prior Publication Data

US 2009/0038390 A1 Feb. 12, 2009

Related U.S. Application Data

(63) Continuation-in-part of application No. PCT/IL2007/000118, filed on Jan. 31, 2007.

(60) Provisional application No. 60/763,395, filed on Jan. 31, 2006.

(51) Int. Cl.
*E21B 49/10* (2006.01)
(52) U.S. Cl. .................................... 73/152.25
(58) Field of Classification Search ......... 73/73, 152.06, 73/152.25, 152.26
See application file for complete search history.

(56) References Cited

U.S. PATENT DOCUMENTS

| | | | | |
|---|---|---|---|---|
| 2,301,624 A * | 11/1942 | Holt | ............ | 166/100 |
| 2,441,894 A * | 5/1948 | Mennecier | ............ | 166/63 |
| 2,581,070 A * | 1/1952 | Blood | ............ | 166/100 |
| 4,484,626 A | 11/1984 | Kerfoot et al. | | |
| 5,465,628 A | 11/1995 | Timmons | | |
| 5,549,159 A * | 8/1996 | Shwe et al. | ............ | 166/250.02 |
| 5,644,947 A | 7/1997 | Hubbell et al. | | |
| 6,263,726 B1 * | 7/2001 | Hubbell et al. | ............ | 73/73 |
| 6,283,209 B1 | 9/2001 | Keller | | |
| 6,615,653 B1 * | 9/2003 | Hocking | ............ | 73/152.01 |
| 6,729,399 B2 * | 5/2004 | Follini et al. | ............ | 166/264 |
| 6,742,405 B2 * | 6/2004 | Hubbell et al. | ............ | 73/863.23 |
| 6,761,076 B1 * | 7/2004 | Hubbell et al. | ............ | 73/864.52 |
| 6,956,381 B2 | 10/2005 | Dahan | | |
| 7,699,124 B2 * | 4/2010 | Corre et al. | ............ | 175/60 |
| 7,874,356 B2 * | 1/2011 | Corre et al. | ............ | 166/187 |
| 2007/0151724 A1 * | 7/2007 | Ohmer et al. | ............ | 166/187 |
| 2007/0260439 A1 * | 11/2007 | Keller | ............ | 703/10 |
| 2008/0142214 A1 * | 6/2008 | Keller | ............ | 166/250.01 |
| 2009/0095066 A1 * | 4/2009 | Keller | ............ | 73/152.28 |

FOREIGN PATENT DOCUMENTS

EP 1 316 674 6/2003

OTHER PUBLICATIONS

International Search Report for PCT/IL2007/000118, mailed Jun. 12, 2007.
Written Opinion for International Application No. PCT/IL2007/000118, mailed Jun. 12, 2007.

* cited by examiner

*Primary Examiner* — John Fitzgerald
(74) *Attorney, Agent, or Firm* — Nixon & Vanderhye P.C.

(57) ABSTRACT

The present application is directed to a method and apparatus for monitoring soil hydraulic properties, and for collecting soil pore-water samples, in relatively undisturbed soil conditions, by means of a vadose zone probe (10) adapted to be mounted on an inflatable sleeve (18) for installation in a borehole (14) formed in the vadose zone, said vadose zone probe comprises a fluid cell (15) having one or more conduits (13*a*, 13*b*, 13*c*) connected thereto for externally accessing its interior, and a porous medium (11) installed in, or formed on, one of its walls for allowing passage of liquid between the interior of said fluid cell and the borehole soil, wherein said vadose zone probe is made from an elongated body having a front (10*f*) and rear (10*r*) sides, and wherein said rear side is substantially flat and said front side is made from a deformable and permeable material, or having a curvature corresponding to the curvature of said borehole.

23 Claims, 8 Drawing Sheets

METHOD AND SYSTEM FOR MONITORING SOIL PROPERTIES

This application is a Continuation-in-Part to International Application No. PCT/IL2007/000118, filed 31 Jan. 2007, which designated the U.S. and claims priority to U.S. Provisional Patent Application No. 60/763,395, filed 31 Jan. 2006, the entire contents of each of which are hereby incorporated by reference.

FIELD OF THE INVENTION

The present invention relates to the study and analysis of chemical and hydraulic properties of the ground. More particularly, the invention relates to a method and apparatus for monitoring the properties of soil and of pore-water in the vadose zone.

BACKGROUND OF THE INVENTION

The monitoring of ground chemical and hydraulic properties is advantageously employed in different applications, such as for example, monitoring pore-water and ground contamination, irrigation control systems of agriculture crops, and for the study of soils and plants. For this purpose special tools are needed to provide accurate information on the fluids contained in the ground, and for monitoring the chemical properties of the water and/or contaminants percolating therein. The monitoring of the vadose zone, which is the layer of land above the zone of saturation (i.e., above the water table), is of particular interest in such applications. The vadose zone connects sources of on land surface pollution with the groundwater in the saturation zone, such that real-time monitoring of the vadose zone may substantially assist in controlling groundwater quality.

Instruments such as tensiometers and suction cups are commonly used nowadays to measure the soil water potential, and to obtain samples of soil pore-water. These instruments are based on the generation of hydraulic continuity between the soil pore-water and water within a cell, through a porous medium (such as porous ceramic, porous metal or porous polymer). While, tensiometers and suction cups may be effectively used in soil science and agricultural practice, their use is relatively limited to very shallow soil depths. Typically, the porous tip, which is usually made of brittle ceramic material, is pushed into the ground, if the soil is soft enough, or installed in a small-diameter hole specially drilled for that purpose, and thus these devices can not be used to collect information from deeper ground layers in the vadose zone.

U.S. Pat. No. 6,956,381 discloses a method and system for measuring permittivity and electrical conductivity in deep soil levels using a flexible TDR (time domain reflectometry) probes attached to the outer side of a flexible sleeve disposed in a borehole. The flexible sleeve is sealed to prevent leakage of a filling material, such that improved contact of the TDR probes with the walls of the borehole is obtained after placing said sleeve in the borehole and filling it with said filling material.

The methods described above provide solutions for continuous monitoring of the ground water content in deep sections of the vadose zone. Though water content is one of the most important hydraulic parameter required for the study of hydrological process in the vadose zone it is most important to have a method that would enlarge the range of monitored parameters and add real time information on the ground water potential and pore water chemical properties. Therefore there is still a need for suitable means for sampling and monitoring chemical and hydraulic properties in deep soil levels.

It is therefore an object of the present invention to provide a method and apparatus for collecting real-time continuous information from deep vadose zone layers.

It is another object of the present invention to provide a method and apparatus for monitoring infiltration processes in deep soil levels, and for determining the hydraulic conditions and chemical properties of the percolating water.

It is a further object of the present invention to provide sampling probes configurations adapted for installation in deep soil levels.

It is yet another object of the present invention to provide a method and apparatus which allow real time monitoring of contaminant migration in the vadose zone while enabling to obtain pore water samples from various depths for chemical analysis and measure the ground water potential.

Other objects and advantages of the invention will become apparent as the description proceeds.

SUMMARY OF THE INVENTION

It has been found that it is possible to continuously collect liquid samples from, and monitor the hydraulic properties of, the vadose zone deep layer by means of one or more vadose zone probes mounted on an inflatable flexible sleeve adapted for installation in a borehole formed in the vadose zone, wherein each of said vadose zone probes comprises a fluid cell having one or more conduits connected thereto for externally accessing its interior, and a porous medium (e.g., porous ceramic, porous metal or porous polymer) installed in, or formed on, one of its walls for allowing passage of liquid between the interior of said fluid cell and the borehole soil (i.e., the soil contacting said porous medium). During the installation of the inflatable sleeve and the vadose zone probes mounted thereon, said inflatable sleeve is lowered into the borehole and then inflated therein such that a continuous pressure is applied over said one or more vadose zone probes, thereby pressing them against the wall of the borehole and obtaining hydraulic continuity between water contained in the soil and water contained in the interior of said fluid cell through said porous medium.

The vadose zone is the layer of land above the zone of saturation. The borehole in which the vadose zone probes of the invention are installed is a vertical or slanted borehole drilled across the vadose zone by means of conventional drilling equipment. Whenever the term external is used herein with conjunction with elements/means of the invention, it generally meant to refer to elements/means located on the land surface external to said borehole.

The term hydraulic continuity used herein generally refers to the interconnection between water contained in a fluid vessel and water contained in the soil. Said water interconnection is typically obtained through a permeable medium assembled, or formed, on one of the walls of said fluid vessel.

The inflatable sleeve may be any type of flexible sleeve capable of receiving a volume of filling material and expand radially in effect, said sleeve is preferably made from a flexible liner made from any type of suitable flexible material, such as, but not limited to, PVC, rubber, polyethylene, Teflon, or enforced fabric, where said filling material may be a type of gas, liquid, solidifying liquid (e.g. two-component urethane, concrete, epoxy resin, foaming material) or dry sand, preferably, a type of solidifying liquid, such as but not limited to, two-component urethane or concrete.

Other types of probes/sensors may be also mounted on the inflatable sleeve such that they contact the borehole wall and collect additional information therefrom, that may be used in conjunction with the information obtained via vadose zone probes of the invention. For example, a TDR probe may be mounted on the inflatable sleeve in proximity to each vadose zone probe for measuring the moisture of the soil in the area of the vadose zone probe.

The fluid cell may be equipped with one or more sensing means electrically connected to external monitoring device(s) by means of conducting lines passing along, inside or external to, the flexible sleeve. The sensing means may include, but not limited to, a pressure sensor for measuring the pressure in the fluid cell and liquid level sensing means for monitoring the liquid level in said fluid cell, or specific analytical electrodes such as pH, Redox, EC, Oxigen, Nitrate, etc.

After the inflatable sleeve is inflated in the borehole such that the vadose zone probes (and any additional probe(s)/sensor(s) that may be) mounted thereon are pressed against the wall of the borehole, the interiors of the fluid cells are filled with a volume of water via the one or more conduits connected thereto, and hydraulic continuity between the water contained in the fluid cell and the pore-water in the soil is achieved via the porous mediums of said fluid cells. The one or more conduits accessing the interior of each fluid cell may be used for collecting samples of the liquid obtained therein, for applying positive/negative pressure conditions therein. The potential of said liquid may be measured by means of a pressure sensor installed therein, and the level of said liquid may be controlled by means of liquid level sensing means and said one or more conduits.

Accordingly, in a first aspect, the present invention relates to a method for determining the quality and/or purity of the ground pore-water in the vadose zone, the method comprises:
   drilling a borehole across a section of the vadose zone;
   lowering into said borehole an inflatable sleeve comprising one or more vadose zone probes mounted thereon, said inflatable sleeve adapted to be installed in a borehole formed in the vadose zone, and each of said vadose zone probes comprises a fluid cell having one or more conduits connected thereto for externally accessing its interior, and a porous medium installed in, or formed on, one of its walls for allowing passage of liquid between the interior of said fluid cell and the soil contacting it;
   filling said inflatable sleeve with a filling material such that a continuous pressure is applied over said one or more vadose zone probes, thereby pressing them against the wall of the borehole and obtaining hydraulic continuity between the soil contacting the porous medium of said one or more vadose zone probes and the interior of their fluid cells through said porous medium;
   introducing a volume of liquid into said fluid cells via said one or more conduits; and
   whenever needed, removing volumes of liquid from said fluid cell via said one or more conduits.

The method may further comprise measuring the pressure in said fluid cell by means of pressure sensing means installed in the fluid cells of the one or more vadose zone probes, wherein said measuring is carried via conducting wires electrically connected to said pressure sensing means. Furthermore, additional information may be collected via additional probe(s)/sensor(s) that may be mounted on the inflatable sleeve.

The level of the liquid contained in the fluid cells may be continuously controlled by means of liquid level sensing means that may be installed thereinside such that whenever the level of liquid in a fluid cell exceeds some predetermined upper threshold (e.g., $30\% \leq$ [upper threshold] $\leq 100\%$) a volume of liquid is removed therefrom via said one or more conduits, and whenever the level of liquid in a fluid cell is beyond some predetermined lower threshold level (e.g., $0\% \leq$ [lower threshold] $\leq 30\%$) a volume of liquid is introduced thereinto via said one or more conduits.

Furthermore, pressure/vacuum conditions may be applied in the fluid cell by means of any suitable pressure source (e.g., pressure pump or compressed gas) connected to one of said one or more conduits.

The passage through said one or more conduits may be controlled by means of controllable valves installed thereon in proximity to the fluid cell.

In another aspect the present invention is directed to a probe for continuously collecting liquid samples from, and monitoring the hydraulic properties of, the vadose zone, said probe (hereinafter vadose zone probe) is adapted to be mounted on an inflatable sleeve for installation in a borehole formed in the vadose zone, said vadose zone probe comprises a fluid cell having one or more conduits connected thereto for externally accessing its interior, and a porous medium installed in, or formed on, one of its walls for allowing passage of liquid between the interior of said fluid cell and the soil contacting it, wherein said inflatable sleeve is inflated in said borehole by means of a filling material such that said vadose zone probe mounted thereon is pressed against the wall of the borehole and hydraulic continuity between the water contained in the interior of said fluid cell and water contained in the soil is obtained via said porous medium.

The vadose zone probe is preferably made from an elongated body having a front and rear sides, said rear side is substantially flat and said front side is made from a deformable and permeable material, or alternatively, it is made more or less curved about its length, for increasing the surface contact between said front side and the borehole wall, and slanted ends configured in an acute angle to said front side such that said vadose zone probe may be anchored in place in response to a pressure applied over said rear side and slanted ends due to a filling material introduced into said inflatable sleeve.

The fluid cell is preferably an elongated fluid container configured to be installed in the vadose zone probe and having a porous medium installed in, or formed on, one of its walls and allowing passage of liquid therethrough. The one or more conduits accessing the interior of said fluid cell may be used for introducing or removing volumes of liquid therefrom, and/or for applying positive/negative pressure conditions thereinside. Preferably, at least one conduit is used for introducing or removing liquid from said fluid cell, and at least one other conduit is used for applying positive/negative pressure conditions thereinside.

According to one preferred embodiment of the invention the porous medium is attached in, or over, an opening formed in a wall of the fluid cell facing the front side of the vadose zone probe such that the outer surface of said porous medium aligns with, or slightly protrudes from, the surface of the front side of said vadose zone probe such that said outer surface can efficiently contact the borehole soil when said vadose zone probe is pressed against its wall. Advantageously, the outer surface of said porous medium is curved about its length in order to maximize its surface contact with the curved wall of the borehole.

According to another preferred embodiment of the invention the porous medium is provided in a form of an elongated cup having a cavity and an opening which opens through the base of the fluid cell into its interior, wherein at least the portion of said fluid cell comprising said porous medium is covered with a permeable and deformable medium for establishing hydraulic continuity between water contained in the interior of said fluid cell and water contained in the soil contacting said vadose zone probe via said porous medium and said permeable and deformable medium. Preferably, said permeable and deformable medium is implemented by enclosing at least a portion of said fluid cell comprising said porous medium with a net and a grainy material filling the space between said net and said portion of said fluid cell. Said grainy material is preferably comprised of fine soil particles, wherein the pores in said net are preferably small enough to hold said fine soil, while allowing limited passage thereof therethrough whenever it is pressurized.

Alternatively, the permeable and deformable medium is made of a material selected from the group consisting of: porous plastics, sponges, clay, and very soft porous polymers.

An external pressure source connected to one of the one or more conduits may be used for applying positive/negative pressure conditions in the fluid cell. Said pressure source, and any sensing means which may be installed in the fluid cell, may be linked to an external control device adapted to receive inputs from said sensors and provide control signals for operating said pressure source.

The passage through the one or more conduits may be controlled by means of controllable valves installed thereon and electrically linked to an external control device via respective control lines. Preferably, said controllable valves are installed on said conduits external to, and in proximity to, the fluid cell.

In yet another aspect the present invention is directed to a system for determining the quality and/or purity of soil and pore-water in the vadose zone, the system comprises:
an inflatable sleeve adapted to be installed in a borehole formed in the vadose zone; and
one or more vadose zone probes mounted on said inflatable sleeve, said vadose zone probes comprises a fluid cell having one or more conduits connected thereto for externally accessing its interior, and a porous medium installed in, or formed on, one of its walls for allowing passage of liquid between the interior of said fluid cell and the soil contacting it.

The porous medium may be provided in the form of a cup having a cavity, said cup is attached to the base of the fluid cell such said cavity opens into the interior of said fluid cell. Advantageously, at least a portion of the fluid cell comprising said porous medium is covered by a permeable and deformable medium, said permeable and deformable medium may be implemented by a net and a grainy material filling the space between said net and said portion of said fluid cell.

The system may further comprise other types of probes/sensors mounted on the inflatable sleeve such that they contact the borehole wall and collect additional information therefrom, that may be used in conjunction with the information obtained via the vadose zone probes of the invention.

BRIEF DESCRIPTION OF THE DRAWINGS

The present invention is illustrated by way of example in the accompanying drawings, in which similar references consistently indicate similar elements and in which.

DETAILED DESCRIPTION OF PREFERRED EMBODIMENTS

The present invention is primarily directed to a method and apparatus for monitoring soil hydraulic properties, such as soil water potential, and for collecting soil pore-water samples, in relatively undisturbed soil conditions. While the apparatus of the invention is particularly useful in the monitoring of soil pore-water in the deep vadose zone, it is not limited to the deep vadose zone and can be equally used in shallow soil horizons. Furthermore, as will be appreciated by those skilled in the art the method and apparatus of the present invention are also suitable for monitoring of other soil solutions and liquids, such as, but not limited to, dissolved constituents in aqueous phase such as dissolved organic and inorganic substances, non aqueous phase substances, such as hydrocarbons and fuels.

As will be appreciated the vadose zone monitoring apparatus of present invention may be advantageously used to produce alerts concerning groundwater contamination. The dynamic processes controlling the chemical properties of the percolating water and transported pollution in the vadose zone highly depends on the temporal variation in the physical, chemical and microbiological conditions of the subsurface. Accordingly groundwater contamination may be reduced and/or controlled to some extent if contamination is detected early enough. Any remediation action in the vadose zone essentially requires on line, real time, continuous monitoring of the chemical and physical properties of the ground pore water, and as will be recognized from the following description the method and apparatus of the present invention are particularly advantageous for such purposes.

The apparatus of the present invention utilizes a vadose zone sampling probe, and special installation techniques, specially designed to allow installation of several such probes along a cross-section of the deep vadose zone. The monitoring system of the invention is designed to be installed in an uncased borehole. While standard sampling ports using a porous tip (e.g., tensiometers) are designed to be pushed into the ground, the vadose zone probe of the invention is specially designed to allow pressing it against the wall of a borehole in order achieve surface contact with the vadose zone soil and hydraulic continuity therewith.

The configuration of the vadose zone probe of the invention is based on attachment of a porous medium of the vadose zone probe to the borehole wall using a special inflatable sleeve designed to be lowered into a borehole and then inflated, which in turn presses the vadose zone probes mounted on the outer side of the inflatable sleeve against the borehole walls. The inflatable sleeve may be implemented by a flexible sleeve made from any suitable flexible material, preferably from a flexible liner, made from PVC, rubber, polyethylene, Teflon, or an enforced fabric, for example.

The length of the inflatable sleeve should be determined according to the depth of the tested vadose zone, which substantially varies over the globe. For example, in current applications flexible sleeve in lengths ranging between 2 to 50 meters were used and installed successfully in the vadose zone of several sites, however, the length of the flexible sleeve is of course not limited to such lengths and much longer flexible sleeves may be needed in other geographical locations. The diameter of the inflatable sleeve may generally be in the range of 5 to 20 cm, but it is of course not limited to these dimensions. Preferably, the diameter of the flexible sleeve is only few centimeters, but it also depends on the depth of the drilled borehole and on the drilling ability. The distal end of the inflatable sleeve is preferably sealed (e.g., by gluing or welding) to ensure pressure generation within the sleeve and prevent leakage of the filling material into the borehole.

Inflation of the inflatable sleeve can be achieved by means of a filling material, such as but not limited to, gas, liquid, solidifying liquid (e.g. two-component urethane, concrete, epoxy resin, foaming material) or dry sand. The filling material is preferably a type of solidifying liquid, such as, but not limited to, two-component urethane or concrete.

Using such solidifying agents to fill the flexible sleeve advantageously generates hydrostatic pressure that can push the probes with substantially great force against the borehole walls, said force is preferably responsive to a pressure which equals to the natural lithostatic pressure (the vertical pressure at a point in the earth crust imposed by the overlying layers of rocks and/or soil), which varies relative to the depth of the probes in the vadose zone. In this way, the contact of the porous medium of the vadose zone probes with the soil is improved, and the natural lithostatical pressures within the drilled borehole are restored. Typically, when a solidifying agent is used, after filling the sleeve the solidifying agent consolidates and the vadose zone probes mounted thereon are permanently placed in a cross-section of the vadose zone.

Another advantage of using a solidifying liquid as a filling material is the healing of tension-release cracks that can potentially be generated by the bore-hole drilling. While the flexible sleeve may be installed in boreholes drilled at any inclination, in a preferred embodiment of the invention the vadose zone probes are attached to the ceiling of a slanted (e.g., in an angle of 30° to 50° to the surface level) borehole in order to provide monitoring of undisturbed soil conditions.

Figures 1, 2, 3:
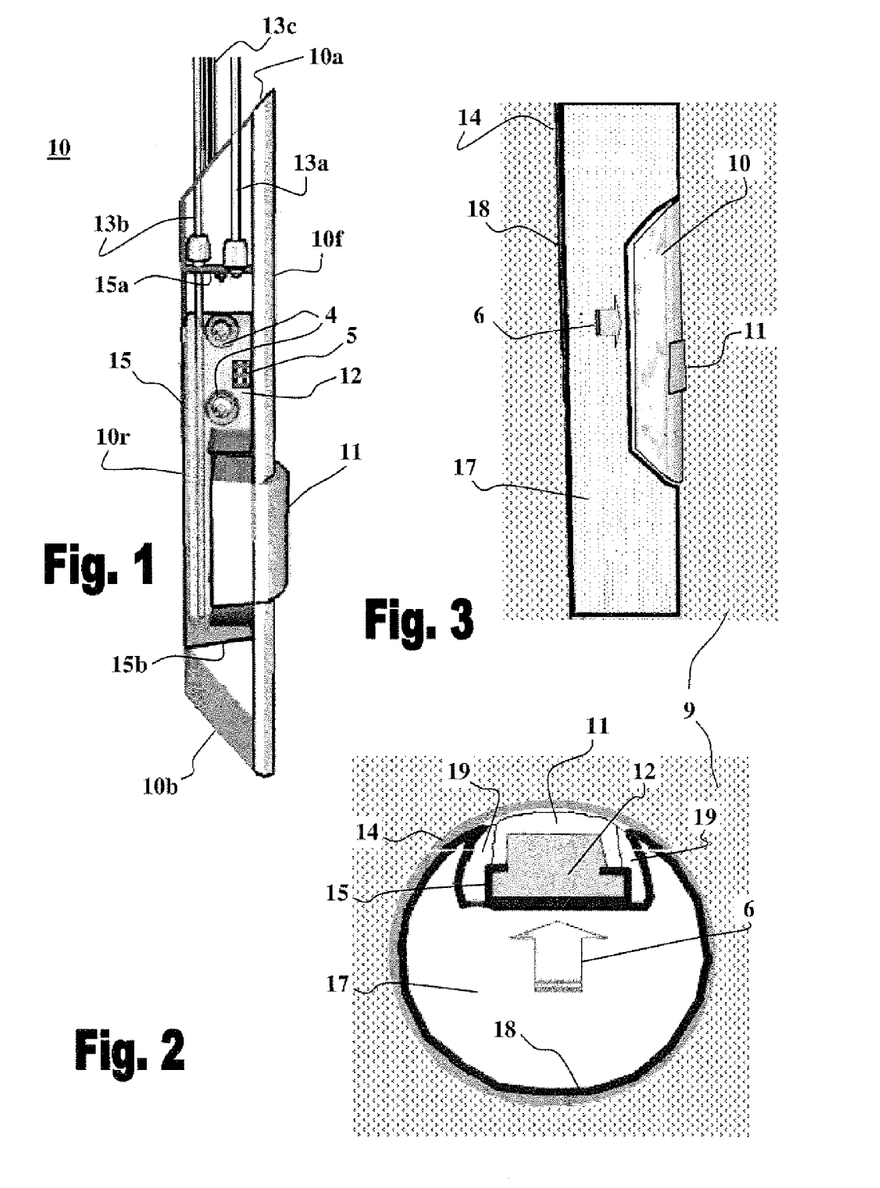
FIG. 1 is a cross-longitudinal view of one preferred embodiment of the vadose zone probe of the invention.
FIG. 2 is a cross-sectional view of the vadose zone probe shown in FIG. 1.
FIG. 3 is a side view illustrating the attachment of the vadose zone probe of the invention to the wall of a borehole by means of an inflatable sleeve.

FIG. 1 is a longitudinal-view of a vadose zone probe 10 designed to be installed in a borehole in direct contact with the borehole wall. Vadose zone probe 10 is generally comprised of an elongated body having slanted extremities 10a and 10b, configured such that a trapezoidal shaped profile is obtained wherein the trapezoid large basis in said profile forms the front face 10f of the vadose zone probe 10. In this way the vadose zone probe 10 can be efficiently pressed laterally by the application of pressure over the surface of the small basis 10r (also referred to herein as the rear face) of its trapezoidal profile and said slanted ends, 10a and 10b, as will be explained herein later.

Vadose zone probe 10 comprises a curved porous medium 11 having a shape corresponding to the borehole radial curvature in order to maximize the surface contact therebetween. As better seen in FIG. 2, curved porous medium 11 is formed on, attached in, or over (e.g., by means of an adhesive 19, such as, but not limited to, epoxy), an opening provided in, the body of a liquid cell 15 of vadose zone probe 10, such that liquid may pass therethrough to/from the interior of fluid cell 15. The front face 10f of the vadose zone probe 10 is preferably also configured in a curved shape corresponding to the curvature of the borehole, in order to maximize its surface contact with the borehole walls.

Vadose zone probe 10 further includes at least two flexible conduits 13a and 13b, connected thereto in fluid flow communication with the interior of liquid cell 15. A first conduit 13a (hereinafter also referred to as pressure conduit) connected to cell 15 is used for applying positive/negative pressure conditions in liquid cell 15. The end of first conduit 13a, terminating in liquid cell 15, preferably terminates near the ceiling 15a of liquid cell 15, such that only a short portion thereof is introduced into liquid cell 15, in order to prevent entry of liquid 12 obtained in liquid cell 15 thereinto. The second conduit 13b (hereinafter also referred to as liquid conduit) is used for introducing/removing volumes of liquid 12 obtained in liquid cell 15, and thus it is introduced along the length of liquid cell 15 and preferably terminates near the floor 15b of liquid cell 15. Conducting lines 13c may be also attached to vadose zone probe 10 for receiving readings from sensing means (4, 5) installed in liquid cell 15, as will be detailed in the following description.

FIG. 3 shows a side view of the vadose zone probe 10 of the invention when installed in a borehole by means of an inflatable sleeve 18. In this arrangement one or more vadose zone probes 10 are mounted on the outer side of inflatable sleeve 18, using any suitable mounting means, such as, but not limited to, adhesives, plastic/nylon restraints, or by sewing suitable pouches thereon, such that the front face 10f of said probes is directed outwardly to contact the walls of the borehole in which it is installed. After the inflatable sleeve 18 comprising the vadose zone probes 10 is inserted into the borehole, it is inflated by a filling material 17 (e.g., urethane), such that the hydrostatic pressure (designated by arrow 6) in the inflated sleeve pushes the vadose zone probes 10 mounted thereon and presses them against the borehole wall 14. In this way the curved porous medium 11 is pressed against the wall of the bore formed in the vadose zone and becomes in direct contact with soil 9.

Figure 4:
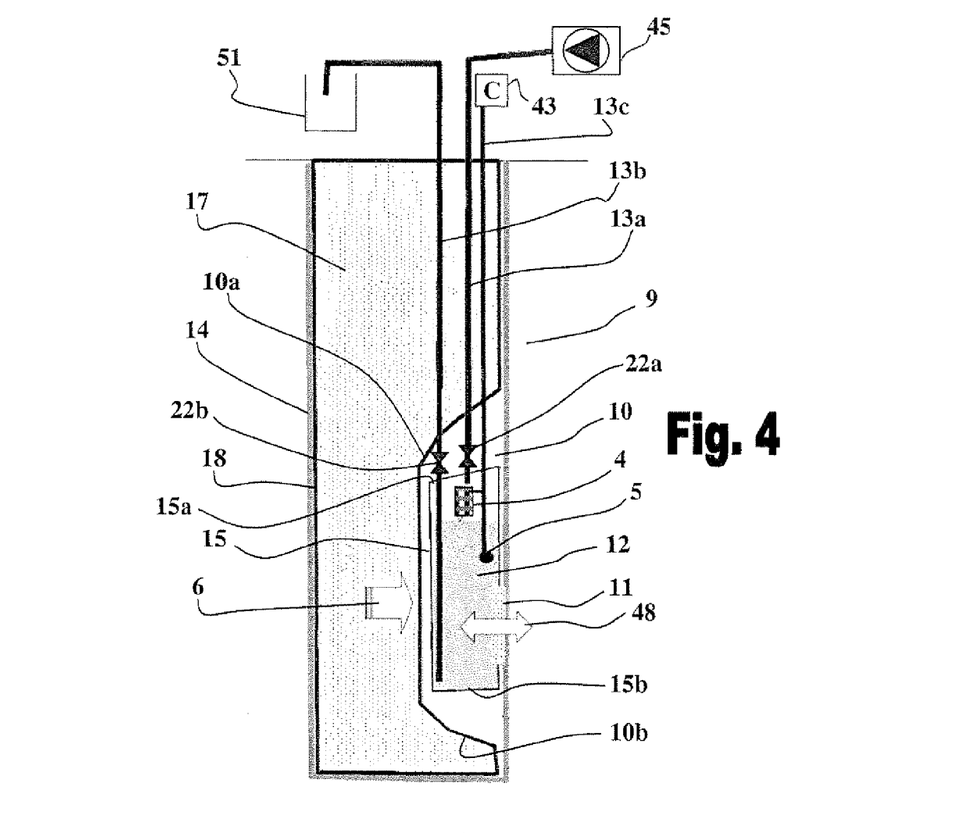
FIG. 4 is a side view of a vadose zone probe of the invention and of the inflatable sleeve.

FIG. 4 is a cross-longitudinal view of a vadose zone probe 10 installed in a borehole by means of a flexible sleeve 18. Vadose zone probe 10 may comprise a pressure sensor 4 and liquid level sensing means 5, connected via conducting lines 13c to an external control (or logging) device 43. Control device 43 may be designed to continuously measure and control the level of liquid 12 in fluid cell 15, by means of liquid level sensing means 5 and pressure source 45 connected thereto via conduit 13a.

For example, if the liquid level measured by liquid level sensing means 5 is below a desired level, control device 43 may generate control signals for operating pressure source 45 to apply vacuum conditions in fluid cell 15 via conduit 13a, which in turn cause suction of liquid from container 51 into fluid cell 15 via conduit 13b. Similarly, if the level of liquid 12 in fluid cell 15 exceeds a predetermined desirable liquid level, control device 43 may generate control signals for operating pressure source 45 to apply pressure conditions in fluid cell 15 via conduit 13a, which in turn cause liquid to eject out of fluid cell 15 into container 51 via conduit 13b.

Similarly, control device 43 may be adapted to continuously, or upon manual initiation of such procedure, obtain liquid samples from fluid cell 15 by operating pressure source 45 accordingly to apply pressure via conduit 13a in order to cause liquid flow via conduit 13b into container 51.

Vadose zone probe 10 may further comprise controllable valves, 22a and 22b, for controllably opening/closing the passage via conduits 13a and 13b, respectively, by means of control signals received from control device 43 via conducting lines 13c. Controllable valves 22a and 22b are preferably assembled on a section of conduits 13a and 13b, respectively, in proximity to fluid cell 15, preferably near its ceiling 15a. Controllable valves 22a and 22b may be used to operate vadose zone probe 10 in various operational modes. For example, when measuring water potential, the controllable valves 22b and 22a may be closed, then the water continuity between the soil 9 and the cell 15 is achieved through porous medium 11 and the pore water pressure in soil 9 may be measured via pressure sensor 4. The water potential may be then determined by continuously measuring the pressure in the fluid cell 15, by means of pressure sensor 4, and determining that pressure equilibrium is reached i.e., constant and stable pressure measurement readings are obtained. In another possible mode of operation solution may be sucked from the soil into vadose zone probe 10 by closing controllable valve 22b, opening controllable valve 22a and activating pressure source 45 to apply negative pressure conditions in fluid cell 15, such that migration of liquid (illustrated by arrow 48) from soil 9 into fluid cell 15 is forced through porous media 11. After reaching a desirable pressure level, as may be measured by liquid level sensing means 5, controllable valve 22a may be closed.

Figure 5:
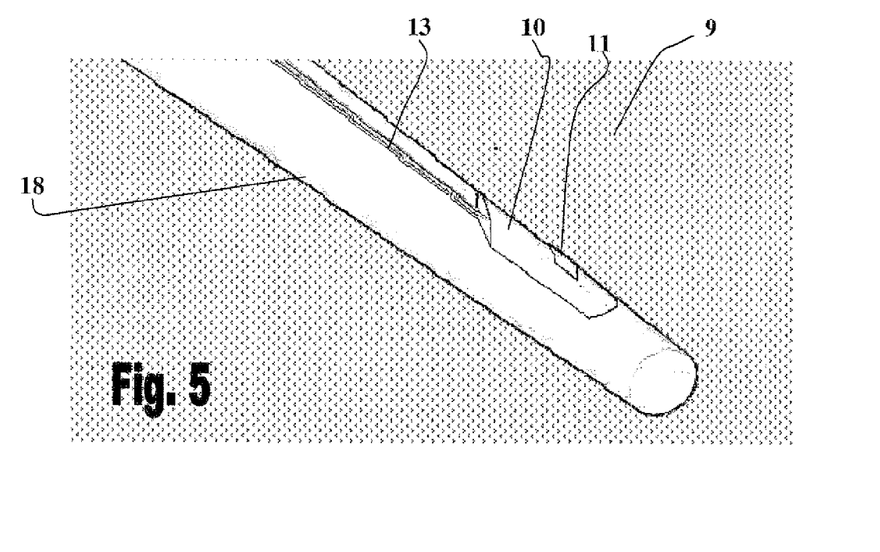
FIG. 5 is a perspective view of the vadose zone probe and inflatable sleeve of the invention

FIG. 5 shows a perspective view of a vadose zone probe 10 mounted on an inflatable sleeve 18 after placing it in a slanted borehole and inflating inflatable sleeve 18. As seen, after inflating sleeve 18 the vadose zone probe 10 and the porous media 11 mounted on its front face are pressed against the upper wall section of the slanted borehole section in which said probe is located.

The body of vadose zone probe 10 may have a truncated cylindrical cross-sectional shape, and it may be made from any suitable type of rigid material, such as, but not limited to, stainless steel, Epoxy mold, Teflon or PVC, preferably from stainless steel. In a specific embodiment of the invention the length of the front face 10f of vadose zone probe 10 may be about 40 cm, the distance between the front and rear faces may be about 8 cm, and the width of vadose zone probe 10 may be about 10 cm.

Fluid cell 15 may be constructed from a hollow elongated vessel having any suitable cross-sectional shape (e.g., cylindrical or rectangular), preferably cylindrical, made from any type of material suitable for holding a volume of liquid thereinside, preferably a type of metal or plastic material, most preferably from stainless steel, Epoxy mold, Teflon, or PVC, and it may be mounted in the body of the vadose zone probe by means of an adhesive material or attached by special structure on the sleeve. In a specific embodiment of the invention the length of fluid cell 15 may be about 25 cm, and its volume may be about 300 cc.

Porous media 11 may be implemented by a plate having a curved face and made from any suitable porous material, such as, but not limited to, porous ceramic or porous metal. In a specific embodiment of the invention the surface area of porous media 11 may be about 100 cm$^2$ (e.g., 10×10 cm), and it may be configured in any suitable geometrical shape (e.g., rectangular, circular) suitable for mounting it in a wall of fluid cell 15. Porous media 11 may cover, or be installed in, an opening formed in the front wall (facing the borehole wall) of fluid cell 15, said opening having more or less the same area and shape of porous media 11. Porous medium 11 is preferably attached to fluid cell 15 using suitable glue, for example, epoxy glue. In a specific embodiment of vadose zone probe 10 the width and height of porous media 11 may be about 10×10 cm.

In specific embodiments of the invention the diameter of a borehole in which flexible sleeve 18 is to be installed is typically in the range of 5 to 20 cm.

Pressure sensor 4 is preferably a type of sensor capable of measuring pressures in the range of 0 to 1 (vacuum) atmospheres, but in specific applications a pressure range of 0 to 2 atmospheres, or a smaller range, may be used. Liquid level sensing means 5 may be implemented by, for example, electrode pairs or optical readers. By way of example, in FIG. 1 the liquid level sensing means 5 is implemented by two electrodes mounted on the wall of the fluid vessel 15. Flexible conduits are preferably made from a type of plastic or metal material, preferably from PVC, stainless steel, or Teflon, having an inner diameter generally in the range of 0.5 to 4 mm, preferably about 1 mm. Control means 43 may be implemented by any suitable controller, or control logic, such as, for example, field computer or data logger.

Pressure source 45 may be implemented by a pressure pump capable of generating either positive or negative pressures, or by a combination of a vacuum pump and pressurized source of gas such as compressed gas. Controllable valves 22a and 22b are preferably a type of two state controllable valves (open/close), such as, for example, letch or solenoids.

The use of the vadose zone probe (10) configuration shown in FIGS. 1 to 5 is suitable for relatively fine particle soils wherein the drilling produces clean smooth borehole walls 14, wherein good surface contact of the curved porous medium 11 and the borehole wall may be easily obtained, which is important for obtaining hydraulic continuity between the soil pore-water and the water 12 contained in the cell 15. Accordingly, the vadose zone probe 10 is less suitable for coarse gravelly soils like alluvial formations, since drilling in such soils results in rough borehole walls that provides poor surface contact between the curved porous medium 11 and the soil of the borehole wall 14.

Figure 6:
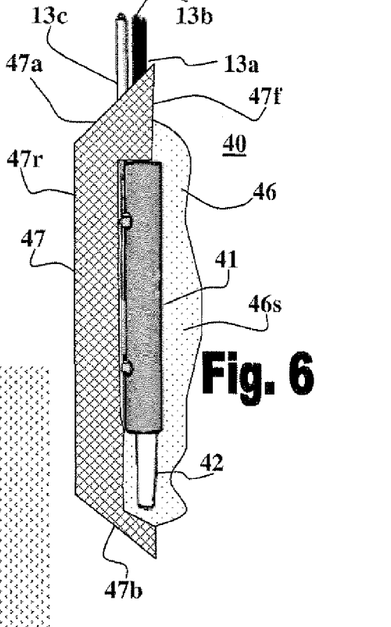
FIG. 6 shows a side view of a vadose zone probe comprising an a permeable and deformable medium.
Figure 7:
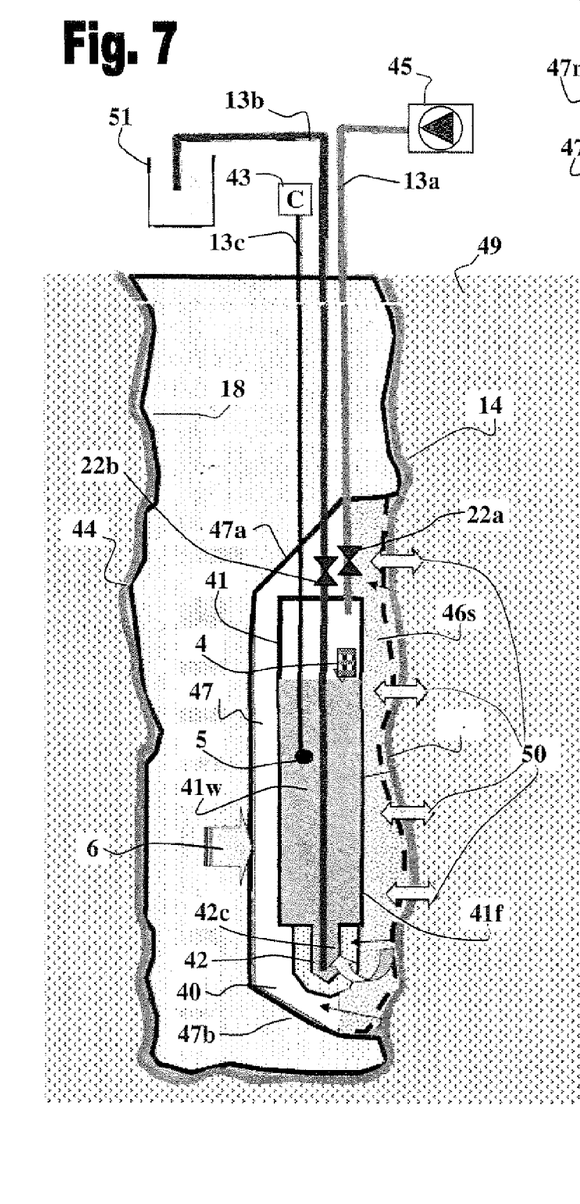
FIG. 7 is a cross-longitudinal view of the vadose zone probe shown in FIG. 6 when installed in a borehole by means of a flexible sleeve.

FIGS. 6 and 7 shows a preferred embodiment of the invention wherein the vadose zone probe 40 is designed for installation in coarse material wherein the drilling produces rough borehole walls 44 (FIG. 7), in which it is difficult to achieve good contact between the solid porous medium and the coarse sediment. In this preferred embodiment the hydraulic continuity between soil in the vadose zone and the fluid cell 41 is achieved by means of a porous tip 42 (e.g., ceramic tip) contained in a permeable and deformable medium 46 (e.g., unconsolidated agent) that can bridge between the coarse soil material 49 and the fluid cell 41 of vadose zone probe 40.

In a specific implementation of the invention vadose zone probe 40 comprises an elongated solid body 47, having a front 47f and rear 47r sides, and slanted extremities, 47a and 47b, configured in an acute angle to said front side 47f, in order to prevent any damage to the inflatable sleeve and for achieving improved anchoring of vadose zone probe 40 due to forces applied over said rear side 47r. The surface of front side 47f, which is more or less flat, comprises a cavity configured to receive fluid cell 41 therein. Fluid cell 41 is preferably made from a cylindrically shaped vessel assembled in the elongated body 47. As demonstrated in FIG. 7 elongated body 47 more or less cover half of the surface area of fluid cell 41 along its length, thereby defining a front face 41f, facing the borehole wall 44, and which is not covered by elongated body 47. The rear side of elongated body 47, which faces the sleeve 18, preferably has slanted extremities 47a and 47b, for anchoring vadose zone probe 40 in place in response to a pressure applied thereover (illustrated by arrow 6) when inflating sleeve 18. The permeable and deformable medium 46 is preferably made in a form of a sand-pillow that intermediate between the front face 41f of fluid cell 41 and the borehole wall 44 through the porous medium 42.

The permeable and deformable medium 46 is preferably made from a flexible fiber net (similar to a mosquito net) that wraps the cell all along its length and filled with very fine wet sand (e.g., having grain size smaller than 0.01 mm) 46s. Advantageously, the cavity in the front side the elongated body 47, in which fluid cell 41 is assembled, is configured such that the porous medium 42 mounted on the base of fluid cell 41 does not contact said elongated body 47. In this way the entire outer surface of porous medium may be surrounded by permeable and deformable medium 46, as demonstrated in FIGS. 6 and 7.

Alternatively, the permeable and deformable medium 46 is made of a material selected from the group consisting of: porous plastics, sponges, clay, or very soft porous polymers.

The installation technique of vadose zone probe 40 is substantially similar to the installation technique previously described hereinabove. In this case, however, once the vadose zone probe 40 is pushed (indicated by arrow 6) against the rough walls 44 of the borehole by the inflated flexible sleeve 18, the permeable and deformable medium 46 is pressed against the wall 44. In a specific embodiment of the invention the permeable and deformable medium 46 is made of a net filled with fine wet sand, while being pressed against the rough wall 44 portions of the sand 46s trapped between said net and the front face 41f of the fluid cell 41 is pushed out of the net holes into the soil cavities thereby providing hydraulic continuity (designated by arrows 50) between the fine sand 46s and the rough soil material 49. The flexibility of the permeable and deformable medium 46 allows it to adjust and fit into the rugged surface of the borehole walls 44 in order to achieve good contact and hydraulic continuity between the fluid cell 41 and the soil 49. An additional advantage in using such permeable and deformable medium is the relatively large surface area which contacts the soil and provides improved conditions for achieving hydraulic continuity in coarse sediments.

The porous tip 42 is preferably made in a shape of a cup connected to fluid cell 41 in fluid flow communication with its interior by attaching it in, or over, an opening provided in the base of fluid cell 41. Advantageously, porous tip 42 is not in contact with elongated body 47, such that its lateral and bottom sides are covered by the permeable and deformable medium for achieving the needed hydraulic continuity. Once the hydraulic continuity between the rough sediments 49 and the fine sand 46s in medium 46 is obtained, then hydraulic continuity between the vadose zone soil and the porous tip 42 is also achieved. As will be appreciated, vadose zone probe 40 is suitable for use in hard rocks wherein achieving substantial surface contact between the surfaces of a solid porous tip 42 and solid rocks is not obvious. The same method may also be applied for fractured rocks where the relatively large area of the permeable and deformable medium may cover large segments of a borehole that is intersected by fractures.

In a specific embodiment the length of the front side 47f of vadose zone probe 40 may be about 40 cm, the distance between said rear and front sides may generally about 6 cm, and the width of vadose zone probe 40 may generally be about 2 cm. Elongated body 47 may be manufactured from any type of suitable rigid material, such as, but not limited to, stainless steel, Epoxy mold, Teflon or PVC, preferably from stainless steel, most preferably it is made from an epoxy mold.

Fluid cell 41 is preferably made from a hollow elongated body (e.g., cylindrical or rectangular) made from any suitable type of rigid material, such as, but not limited to, stainless steel, Epoxy mold, Teflon or PVC, preferably from PVC. In a specific embodiment of the invention the length of fluid cell 41 may generally be about 25 cm, and the volume of its interior in such specific embodiment may be about 100 cc. Porous tip 42 may be manufactured from any suitable porous material, such as, but not limited to, Porous ceramic, porous metal or porous polymer. In a specific embodiment of the invention the length of porous tip 42 may be about 6 cm, and its outer diameter about 2 cm. Fluid cell 41 and porous tip 42 should be designed to withstand pressures in the range of 0 to the hydrostatic pressure needed to elevate water from the depth of the probe, for example it should withstand vacuum pressure of 0.2 typical to dry soils but holds up to 5 bars if the cell is installed at depth of about 40 m.

The interior of fluid cell 41 of vadose zone probe 40 may be accessed via flexible conduits 13a and 13b, preferably passing through the ceiling of fluid cell 41. Pressure conduit 13a is used for applying positive/negative pressure conditions in fluid cell 41, and thus a first end thereof is connected to pressure source 45, while its other end is passed via the ceiling of fluid cell 41 and terminates near said ceiling in order to prevent entry of liquid 41w thereinto. Liquid conduit 13b is used for introducing/removing liquid volumes from the interior of fluid cell 41, and thus its external end is connected to liquid container 51, while its other (inner) end enters fluid cell 41 through its ceiling, passed along its length and terminates in the cavity 42c of porous tip 42.

Vadose zone probe 40 preferably further comprises a pressure sensor 4, liquid level sensing means 5, controllable valves 22a and 22b mounted on flexible conduits 13a and 13b, respectively, and controlling the passage therethrough, all of which are electrically linked to control device 43 via conducting lines 13c. As in the vadose zone probe (10) previously described hereinabove, flexible conduits 13a and 13b and conducting lines 13c passes along the length of flexible sleeve 18, preferably in its interior, and reach land surface where they are connected to the respective external devices i.e., pressure source 45, container 51, and control device 43. The flexible conduits, sensing means, controllable valves, pressure source, and control device, may be similar to those used in the vadose zone probe (10) described hereinabove with reference to FIGS. 1-5.

The vadose zone probes described hereinabove are generally operated in a similar way after installation in the borehole.

In general, flexible conduits 13a and 13b used to access the interior of the fluid cells (15 or 41) and the liquid level sensing means 5 are used for monitoring, maintenance and control of the fluid cell and the liquid contained thereinside. Flexible conduit 13b is generally used for transferring liquid from the land surface to the fluid cell, or vice versa. The inner diameter of flexible conduits is preferably very narrow (e.g., about 1 mm), and the corresponding fittings and conduits used are preferably special vacuum tight accessories. Once the system is installed, hydraulic continuity is achieved either by application of vacuum via flexible conduit 13a, when the soil is wet enough, or by forcing liquid from the fluid cell out to the soil via the porous medium/tip. In order to transfer water from the land surface to the fluid cell, vacuum is applied via pressure conduit 13a and the external end of liquid conduit 13b is introduced into the desired solution in container 51. The vacuum created in the fluid cell (15 or 41) drives the solution in container 51 from the surface via liquid conduit 13*b* into the fluid cell.

The liquid level in the fluid cell may be monitored by means of liquid level sensing means 5, in order to prevent water from entering into the lower end of the pressure conduit 13*a*. Once a desirable level of liquid is obtained in the fluid cell, the vacuum applied via pressure conduit 13*a* may be replaced by a positive pressure (e.g., air or other compressed inert gas) for pushing liquid (12 or 41*w*) from the interior of fluid cell (15 or 41) out to the soil (9 or 49) through the porous medium 11, or through porous tip 42 and sand permeable and deformable medium 46, in order to obtain hydraulic continuity between the liquid obtained in the cell and the soil. Once hydraulic connection is established, pressure sensor (e.g., micro-pressure-transducer—PT), that may be placed either in the fluid cell or on the pressure conduit 13*a*, is used to measure the tension created in the cell. It should be noted that the choice of placing pressure sensor 5 in the fluid cell or in pressure conduit 13*a* should be determined according to the relative volumes of liquid in the cell and gas in the pressure conduit 13*a*. This is one of the reasons for using flexible conduits having relatively narrow internal diameter.

If soil pore-water sampling is desired, then vacuum is applied in the fluid cell via pressure conduit 13*a*, which drives the pore-water in the soil into the fluid cell through the porous medium/tip. Once the fluid cell is filled with the pore-water, as monitored by the level sensing means 5, a positive pressure is applied via pressure conduit 13*a*, which pushes the water through liquid conduit 13*b* over to the land surface. It should be noted that the use of flexible conduits having very narrow inner diameter ensures that all the liquid is pushed all the way up through liquid conduit 13*b* and no liquid drops are left in the conduit, nor is there any bubbling effect that would prevent liquid from flowing all the way up. Since the internal end of liquid conduit 13*b* terminates near the bottom of the fluid cell, or in the cavity of the porous tip, the fluid cell is emptied in a relatively short time (e.g., less then a minute), while the liquid sample makes its way to the surface. Accordingly, only a small amount of liquid is derived back from the cell to the soil.

Figures 8A, 8B:
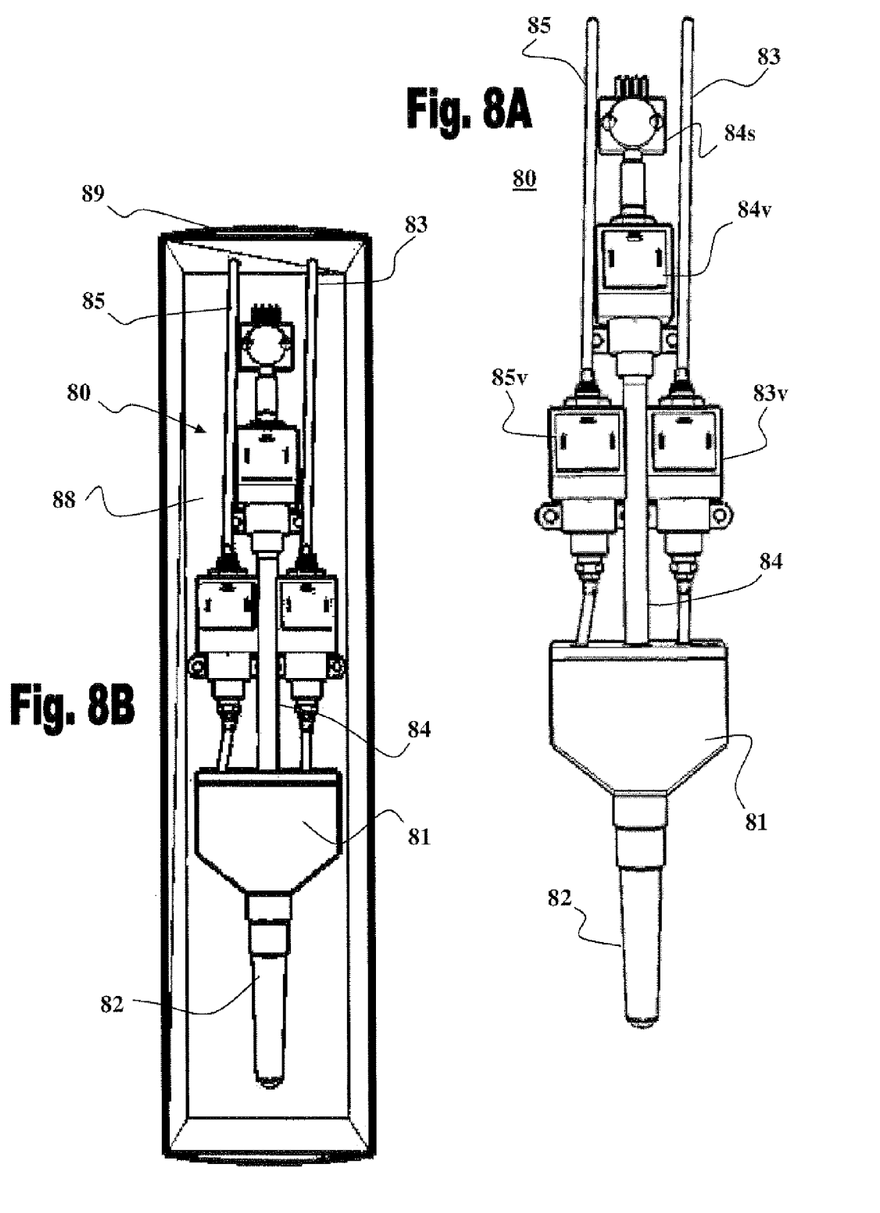
FIGS. 8A and 8B shows front views of a vadose zone probe of the invention having an external pressure sensor.

FIGS. 8A and 8B illustrates another vadose zone probe 80 of the invention, which is designed for installation by means of an inflatable sleeve as previously described herein above, wherein the pressure sensor 84*s* is installed external to fluid cell 81. In this preferred embodiment hydraulic continuity between the interior of fluid cell 81 and vadose zone soil is obtained via a porous tip 82 covered by a permeable and deformable medium 88, as described hereinabove with reference to FIGS. 6-7, and thus it will not be discussed in detail for the sake of brevity. Fluid cell 81 is shown in FIGS. 8A-8B, by way of example, as having generally a rectangular geometrical shape having one tapering side where porous tip 82 is connected, which should not be construed to limit the scope of the invention. Of course, fluid cell 81 may assume any other suitable geometrical shape.

As in the previously discussed embodiments, the interior of fluid cell 81 may be accessed via pressure conduit 83 and liquid conduit 85, connected to the respective pressure source and container (not shown), and the passage thorough said conduits may be controlled by means of respective controllable valves, 83*v* and 85*v*, mounted thereon proximal to fluid cell 81.

The interior of fluid cell is also in contact with an auxiliary conduit 84, which is a relatively short conduit (e.g., few centimeters) having a pressure sensor 84*s* installed on its upper end and a controllable valve 84*v* mounted on said auxiliary conduit 84 near said pressure sensor 84*s*. The operation of controllable valve 84*v* in controlled by an external control device (not shown) to protect pressure sensor 84*s*, such that the passage through auxiliary conduit 84 is blocked whenever extreme pressure is applied in conditions which may evolve in fluid cell 81 during retrieval of water samples therefrom.

As shown in FIG. 8B, vadose zone probe 80 further comprises housing 89 having the shape of an open box in which the elements of the probe are installed. The interior of housing 89 is filled with solidifying resin to achieve rigidity and reinforce the probe. By way of example, the interior of housing 89 may be filled with an epoxy resin. The solidifying resin may cover most of the components of vadose zone probe 80, but should leave at least a portion of the porous tip 82 uncovered. Preferably, most of the surface area of porous tip 82 is left uncovered by said solidifying resin.

The opening of housing 89 is covered by a permeable and deformable medium, such as, but not limited to, a grainy material comprised of fine soil particles, and said opening is preferably covered by a net (e.g., having pores size in the range of 1 to 3 mm) attached over said opening of housing 89 such that a pillow-like face is obtained. Said pillow-like face is adapted to contact the wall of the borehole during installation, assume its surface shape, and thereby achieve maximal surface contact therewith and improved hydraulic continuity. Alternatively, the outer face of housing 89 is covered by a permeable and deformable medium made of a material selected from the group consisting of: porous plastics, sponges, clay, and very soft porous polymers.

Figures 9A, 9B:
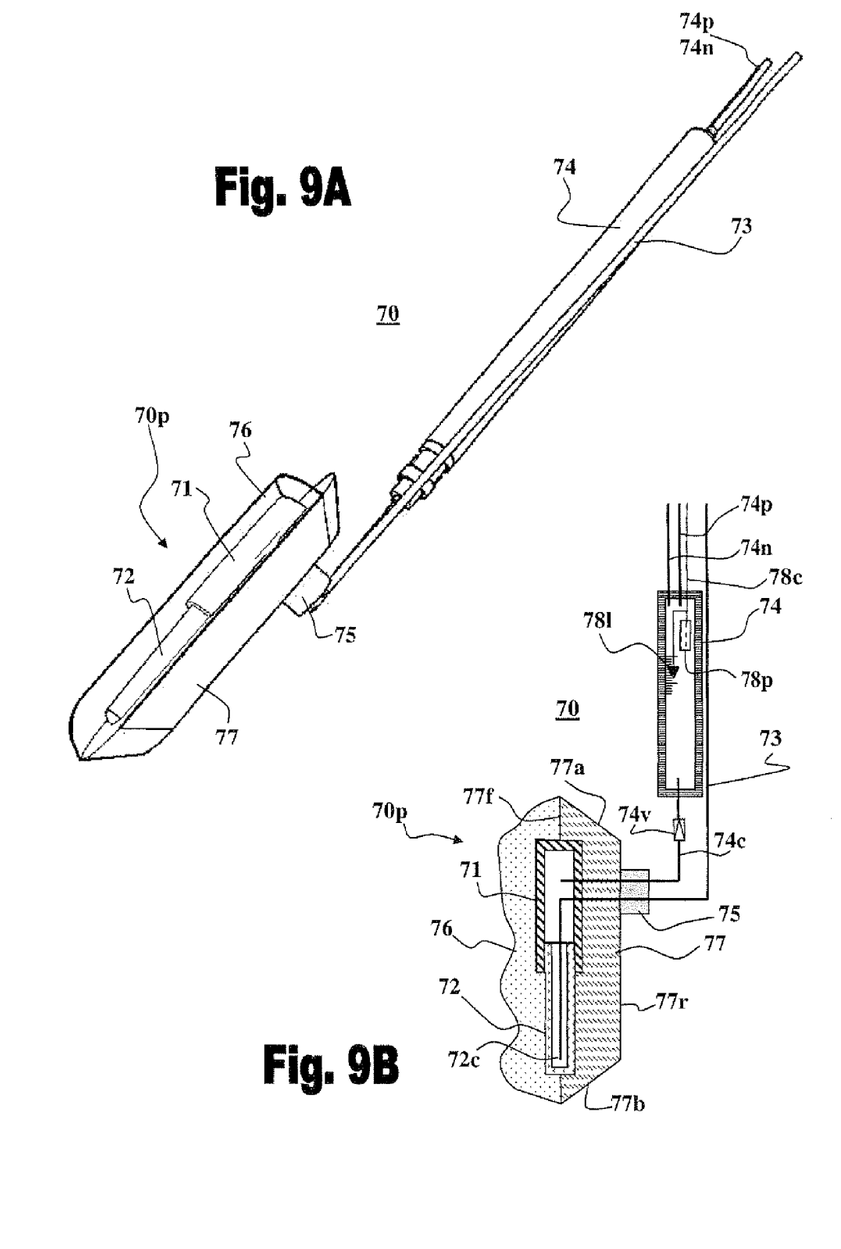
FIGS. 9A and 9B shows a perspective and cross-longitudinal views, respectively, of a vadose zone probe of the invention having an auxiliary cell.

FIGS. 9A-9B shows perspective and cross-longitudinal views, respectively, of yet another vadose zone probe of the invention designed for installation by means of an inflatable sleeve as previously described herein above. In this preferred embodiment of the invention the vadose zone probe is divided into two portions: i) a sampling port 70*p*; and ii) an auxiliary cell 74, which are connected by means of a pressure conduit 74*c*, wherein said sampling port 70*p* is mounted on the inflatable sleeve (not shown) and said auxiliary cell 74 is preferably maintained inside said sleeve. In this arrangement the dimensions of the sampling port 70*p* are substantially reduced by using auxiliary cell 74 to provide an intermediate volume for fluid cell 71.

As in the previously described embodiments (vadose zone probes 40 and 80) hydraulic continuity between the interior of fluid cell 71 and the vadose zone soil is obtained via a porous tip 72 (e.g., ceramic tip) connected to an opening provided in the base of fluid cell 71 and a deformable and flexible medium 76 covering said porous tip 72. Sampling port 70*p* comprises an elongated solid body 77 having a rear side 77*r* being shorter in length than front side 77*f* thereof, thus forming slanted lateral sides (77*a*, 77*b*) which assists in anchoring sampling port 70*p* in place when inflating the inflatable sleeve. Fluid cell 71 and the porous tip 72 connected to its base are attached to the front side 77*f* of body 77, preferably by way of molding.

Body 77 may cover about half of the surface areas of fluid cell 71 and porous tip 72 along their lengths, such that surface areas thereofs which are not covered by solid body 77 may be covered by a permeable and deformable medium 76, as shown in FIGS. 9A and 9B. Permeable and deformable medium 76 should cover the entire surface area of porous tip 72 not covered by body 77, while the surface area of fluid cell 71 not covered by body 77 may be partially covered by said permeable and deformable medium 76, or not covered by it at all.

Permeable and deformable medium 76 may be implemented using a flexible fiber net (similar to a mosquito net) attached to the boundaries of front face 77f of body 77 and filling the space between said fiber net and front face 77f with very fine wet sand (e.g., having grain size smaller than 0.01 mm). It should be understood that sampling port 70p of the invention may be configured differently, for example, the entire surface area of fluid cell 71 may be covered by solid body 77, and porous tip 72 and/or solid body 77 may be configured such that surface area of porous tip 72 is left substantially uncovered by body 77.

Alternatively, the permeable and deformable medium 76 is made of a material selected from the group consisting of: porous plastics, sponges, clay, or very soft porous polymers.

With reference to the cross-longitudinal view shown in FIG. 9B, the interior of fluid cell 71 and porous tip 72 of sampling port 70p may be accessed via liquid conduit 73 and pressure conduit 74c passing though a support member 75 attached to the rear side 77r of solid body 77, and through solid body 77. In this implementation liquid conduit 73 is inserted into fluid cell 71 via the side wall covered by solid body 77, passed along its length into the cavity 72c of porous tip 72, and preferably terminates near the floor of said porous tip 72. Pressure conduit 74c is also inserted into fluid vessel 71 via the side wall covered by solid body 77, and it terminates therein, preferably near the ceiling of fluid cell 71.

Auxiliary cell 74 connected to the interior of fluid vessel 71 via pressure conduit 74c, is used as an intermediate volume for applying positive/negative pressures in fluid cell 71. A one way valve 74v is mounted on conduit 74c for restricting the fluid flow direction in pressure conduit 74c such that the only fluid flow direction permitted is from cell 71 to auxiliary cell 74. This arrangement allows liquid sample flow into the internal space of auxiliary cell 74, but prevents its return into cell 71. In this preferred embodiment the volume of the sampled liquids in cell 71 is much smaller (e.g., several milliliters, preferably between 5 to 20 milliliters), which is preferable since the collection of small volumes of liquid samples better reflects fluctuations in the percolating liquids over time, which therefore improves the accuracy of the sampling of the pore water. Additionally, if the probe is installed in great depth of several tens of meters the high pressure needed to push the water up from cell 74 over to land surface would be avoided from the cell 71 and water within cell 71 will not be pushed back to the soil through the ceramic tip 72 during this process. Auxiliary cell 74 may be connected through conduits 74p and 74n to external positive and negative pressure sources, respectively. Of course, in an alternative embodiment a single conduit may be used to connect auxiliary cell 74 to such pressure sources. Auxiliary cell 74 further comprises sensing means—78l for measuring liquid level, and 78p for measuring the pressure, therein. Said sensing means are preferably connected to external control (or logging) device via conducting wires 78c. Said conducting wires 78c are preferably passed inside the inflatable sleeve and exit said sleeve via its external end on land surface. In this way the size of the sampling port 70p is substantially reduced since a significant portion of the volume of fluid cell 71 is provided by auxiliary cell 74 connected thereto.

Controllable valves (not shown) may be installed on the pressure and fluid conduits for externally controlling the passage therethrough. In this implementation positive/negative pressure conditions are applied first in the auxiliary cell 74 and not in fluid cell 71 due to one way valve 74v provided on conduit 74c. The operation of vadose zone probe 70 is substantially similar to the operation of the vadose zone probes previously described hereinabove.

The body of vadose zone probe 70 may be made from any suitable type of plastic or metal material, such as, but not limited to, stainless steel, PVC, Teflon, Polyethylene. In a specific embodiment of the invention the length of the front face 77f of sampling port 70p may be about 15 cm. The distance between said front and rear faces may generally be about 6 cm, and the width of body 77 may generally be about 2 cm.

Fluid cell 71 may be constructed from an elongated hollow vessel having any suitable cross-sectional shape (e.g., cylindrical or rectangular), preferably cylindrical, made from any type of suitable rigid material, such as, but not limited to, stainless steel, Epoxy mold, Teflon or PVC, preferably from PVC, and it may be mounted in the body of the sampling port 70p by means of mold or adhesive. In a specific embodiment of the invention the length of fluid cell 71 may be about 8 cm, and its volume may generally be about 10 cc.

Porous tip 72 may be made from any suitable porous material, such as, but not limited to, porous ceramic, porous metal or porous polymer, preferably from ceramic, formed in a shape of an elongated cup. Porous tip 72 is preferably attached to fluid cell 71 by a suitable adhesive or by molding it thereto. In a specific embodiment of the invention the length of porous tip 71 may generally be about 6 cm, and its outer diameter may generally be about 2 cm.

Auxiliary cell 74 may be constructed from an elongated hollow vessel having any suitable cross-sectional shape (e.g., cylindrical or rectangular), preferably cylindrical, made from a type of rigid material such as, but not limited to, stainless steel or PVC. In a specific embodiment of the invention the length of auxiliary cell 74 may generally be about 45 cm, and its volume may be about 300 cc. Auxiliary cell 74 should be designed to withstand pressures in the range of 0 (vacuum) to positive pressure of few atmospheres, depending on the installation depth.

Pressure conduits (74n, 74p, 74c) are preferably a type of a thin pipe having an inner diameter in the range of 0.5 to 3 mm, preferably about 1 mm, and capable of delivering pressures in the range of 0 (vacuum) to several atmospheres, depending on the planned installation depth.

The sensitivity of the pressure readings, and the time response to pressure changes, are substantially improved in the vadose zone probe of the invention due the controllable valves that are installed on the pressure and liquid conduits. This arrangement allows to isolate the fluid cell volume from the volumes of the conduits connected thereto, and in this way to substantially cancel interfering effects that are introduced due to the volumes of said conduits i.e., prolonged pressure equilibrium times in the fluid cell.

It should be appreciated that the reduced size of sampling port 70p allows using stronger pressure forces during the installation, while reducing the risks of fracturing the brittle porous tip 72 used therein. In addition, the application of high pressures in auxiliary cell 74 will not affect the pressure in cell 71.

The vadose zone monitoring system of the invention may be advantageously used for monitoring soil and pore-water properties in a range of applications wherein continuous monitoring of soil conditions is required. For example, the vadose zone monitoring system of the invention may be used to monitor the soil properties within facilities that store or handle contaminating materials, such as, for example, chemicals compound manufacturers, petrochemical facilities, and gasoline stations.

Although the vadose zone probe of the invention may be operated without any conduits if only measuring of the soil water potential is needed, preferably at least one or more conduits are provided for accessing the interior of the fluid cell of the vadose zone probe. Furthermore, while the vadose zone probes described hereinabove uses at least two conduits (liquid and pressure conduits) for accessing the interior of the fluid cell, it should be understood that the vadose zone probe of the invention may be operated using a single conduit which may alternatingly function as a liquid or pressure conduit.

Example 1

Within the framework of a research project conducted in the city of Ashdod, Israel, the vadose zone monitoring system of the invention including 12 vadose zone probes (10) of the type shown in FIGS. 1-5, mounted on an inflatable sleeve, were installed along a deep vadose cross-section of 21 m in a sand dune formation. The system was installed during May 2005, and results obtained over a two months period are shown in FIG. 11.

In this example land use impact on groundwater recharge of the coastal aquifer was studied using the vadose zone monitoring system of the invention. The study was conducted in urban, agricultural, and open sand dune spaces around the coastal city of Ashdod, Israel. The sand dune study site was instrumented with several independent monitoring FTDR (flexible time domain reflectometry, as described in "*Flexible Time Domain Reflectometry Probe for Deep Vadose Zone Monitoring*", Ofer Dahan et al, Vadose Zone Journal 2:270-275 (2003)) systems and two additional vadose zone monitoring systems using the direct contact probes (10).

Though said two direct contact probe systems were identical, one system was dedicated to pore water sampling and the other for water pressure measurements. The systems were installed spaced apart (by about 6 to 15 m) to prevent any influence of the pore water sampling on the water pressure measurements. The vadose zone in this site is composed of a ~20 m thick of unconsolidated sand dune and sand stone with a single, ~1 m thick, clay layer ~7 m below surface level. The climate is characterized by rainy winters (~500 mm from October to April) followed by dry summers. Since the study site is located on bare sand dunes with no vegetation the recharge process is controlled primarily by direct percolation of intense rain events.

Figure 11:
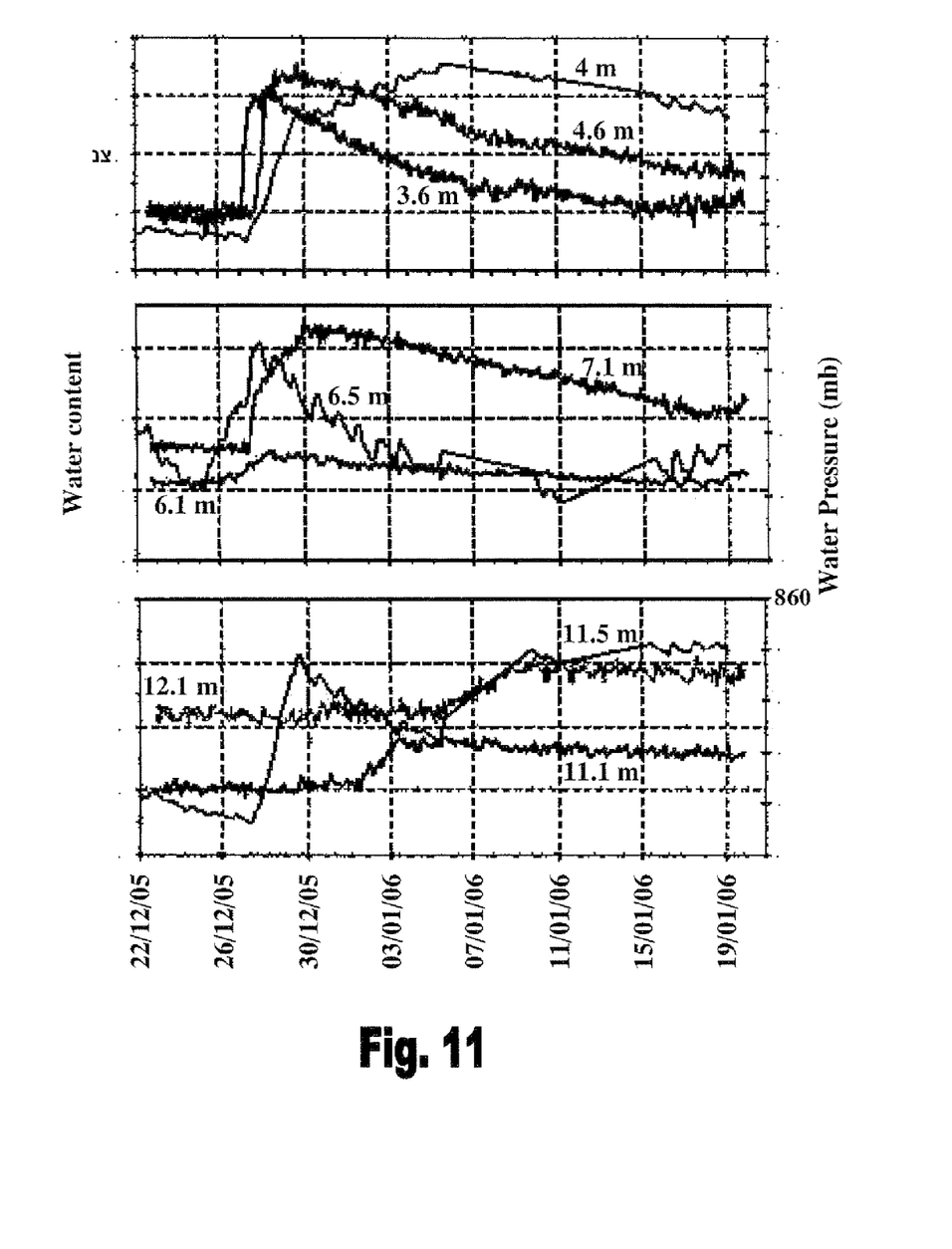
FIGS. 11 and 12 provides plots of results obtained in examples 1 and 2.

Preliminary results from this site, demonstrating pore water pressure response to an infiltration process generated by a rain event, are shown in FIG. 11. The water pressure is measured by the vadose zone probes (10) as absolute pressure (1000 mbar presents atmospheric pressure) at three different depths of 4, 6.5 and 11.5 m below surface level. The water content variation above and below each vadose zone probe was monitored with FTDR probes. As seen in FIG. 11 each monitored wetting process was followed by a water pressure increase. Alternatively, reduction in water content was followed by a water pressure decrease. Deviation from this pattern can be seen on the set of probes that was installed at 11.5 m. Prior to the increase in water pressure that follows the water content increase, a pressure rise is observed with no change in water content. Since the pressure transducers measure absolute pressure it is possible that the pressure rise occurred due to a pressure increase in vadose zone gas phase and not directly as a result of a change in the water tension. The pressure increase may be generated by the infiltration event that, while propagating down the vadose zone, entraps and pressurizes air in the lower layers.

Example 2

Figure 12:
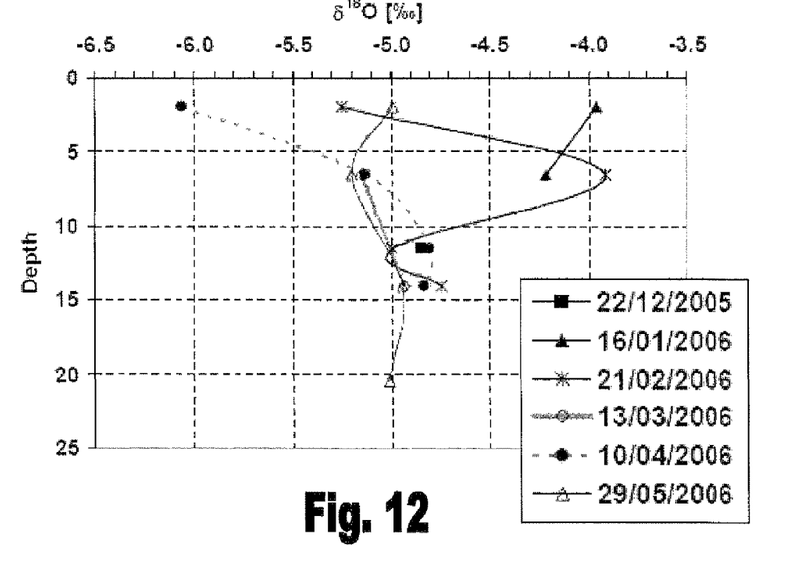

The second vadose zone monitoring system that was installed in this site (the city of Ashdod, Israel) allowed frequent water sampling of pore-water from various depths from land surface to groundwater all along the season. FIG. 12 presents the isotopic composition of the water samples obtained from the vadose zone by the sampling ports in various times and depths. Though the results have significant hydrological meaning it is presented here only to demonstrate the pore sampling capability in various depths.

Figure 10:
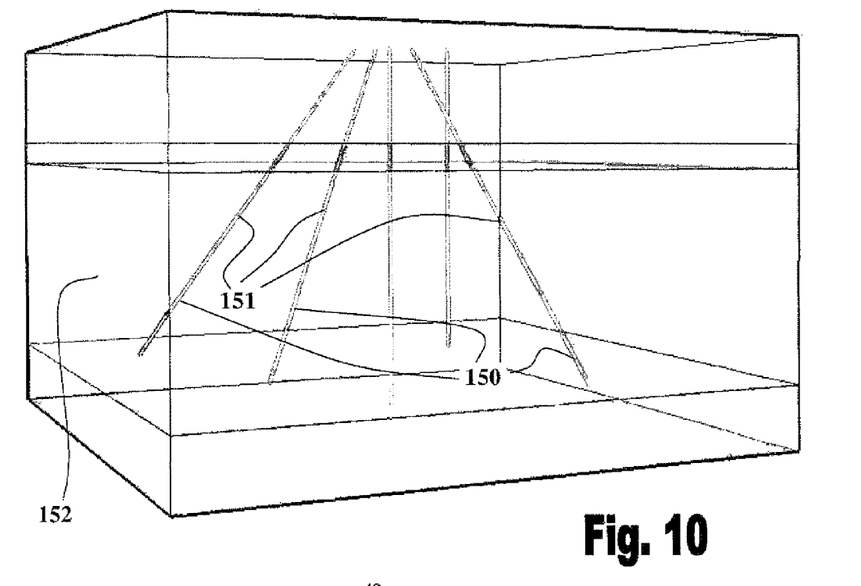
FIG. 10 schematically illustrates the experimental setup used in examples 1 and 2, wherein several flexible sleeves comprising vadose zone probes of the invention were installed in a cross-section of the vadose zone.

FIG. 10 illustrates the experimental setup used in examples 1 and 2, wherein several flexible sleeves 150, comprising vadose zone probes of the invention 151, were installed in a cross-section of the vadose zone 152.

Example 3

Water flow and contaminant transport from land surface to groundwater was investigated in an alluvial formation in the Wadi Arava, Israel. In order to investigate the solute transport pattern, a multi-tracer test was conducted on a section of the stream channel which was instrumented with a vadose zone monitoring system installed during May and August 2005. The system, schematically illustrated in FIG. 13, included five vadose zone probes 40 of the type shown in FIGS. 6-8, used for sampling the percolating water and five FTDR probes 65, used for monitoring the vadose zone wetting process.

Figure 13:
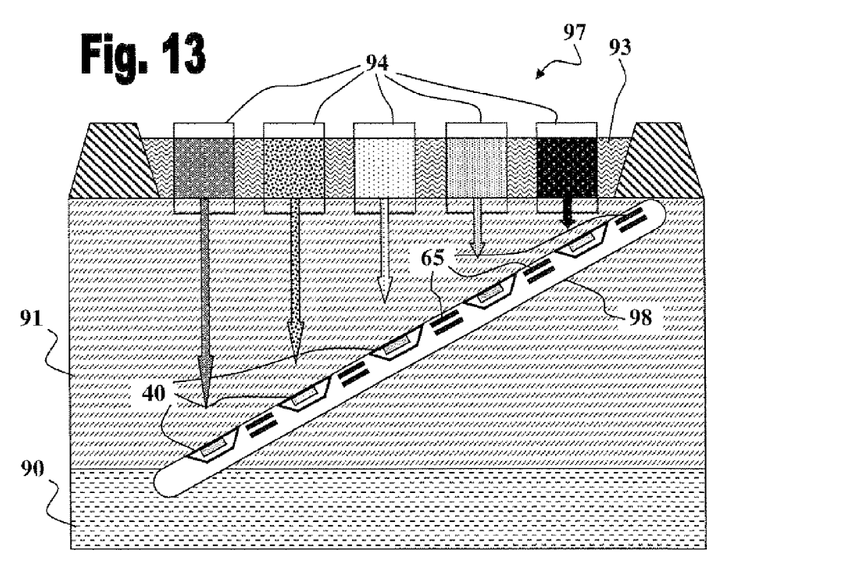
FIG. 13 schematically illustrates an experiment setup carried out using the monitoring system of the invention.
Figure 14:
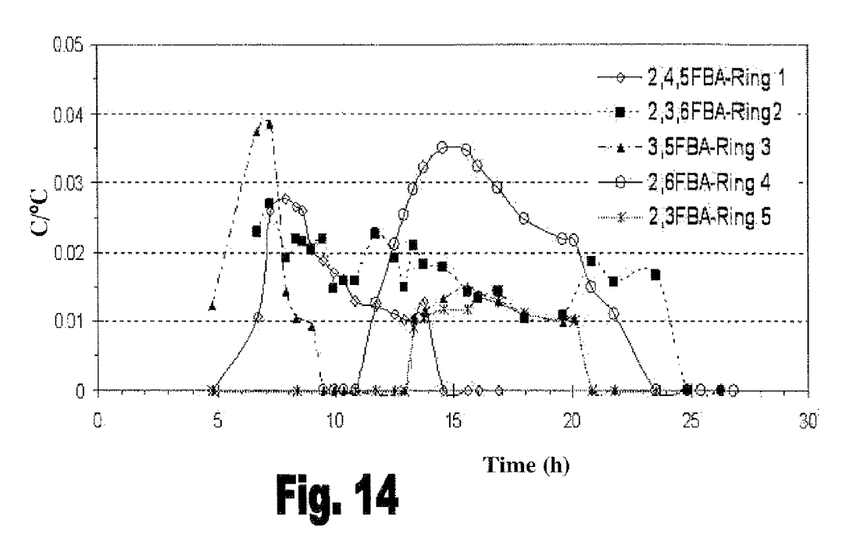
FIG. 14 shows results obtained in example 3.

In this percolation experiment, the vadose zone monitoring system included five vadose zone probes 40 distributed along a 5 m flexible PVC sleeve 98, which was installed in a slanted borehole formed in the vadose zone 91 above the groundwater layer 90. The experiment was conducted through a pond 97 filled with water 93 that was built on the land surface. Five ring infiltrometers 94 were installed on the pond's bottom to allow infiltration of traced solutions contained therein. This experiment was designed to investigate water infiltration mechanisms in alluvial formations. FIG. 14 presents the breakthrough curve of five chemical water tracers (fluorobenzoic acids—FBA) that were injected into the different ring infiltrometers 94 in the pond 97. Similar breakthrough curves of traces obtained from the analysis of water samples retrieved by the vadose zone probes 40 were established. The complete experimental setup and its results reveal interesting information that sheds light on the infiltration process.

Pond 97 was flooded with water 93 to achieve a constant water head. Equal water head between the rings 94 inner side and the pond 97 was maintained throughout the experiment. Water content profile in the vadose zone was continuously monitored by the FTDR system, and the water in the vadose zone probes 40 were frequently sampled. Two tracer tests were conducted in two different sessions, using ten different tracers (five fluorobenzoic acid tracers, Br and Li as ionic tracers and three fluoresces dyes). During each tracer test a certain mass of traced solution in a constant concentration was allowed to percolate through each ring 94. Monitoring of the wetting/draining process by the FTDR system allowed tracing of the wetting front propagation. In addition, analyzing the water samples that were obtained by the vadose zone probes 40 allowed establishment of the breakthrough curves for all tracers in all samples.

FIG. 14 presents the breakthrough curves of the FBA tracers that were injected into the different infiltration rings 94 on the land surface during the first tracer test, in the sampling cell that is located 2.3 m below land surface. The tracer breakthrough curves emphasize the complexity of the infiltration process through layered soil. The graph clearly shows the flow lines mixing pattern, and demonstrates that the flow pattern is far from being vertical. Moreover, some of the tracers appear in the cells with a breakthrough curve that is characterized by two distinct concentration peaks. A multi-peak breakthrough curve is a typical indication of dominancy of a preferential flow mechanism with a dual porosity system. Analysis of the results from all sampling cells in the two tracer tests reveals similar flow behavior.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different vadose zone probes, fluid cells, porous medias and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A vadose zone probe adapted to be mounted on an inflatable sleeve for installation in a borehole formed in the vadose zone, comprising: a fluid cell having one or more conduits connected thereto for externally accessing its interior, and a porous medium installed in, or formed on, one of its walls for allowing passage of liquid between the interior of said fluid cell and the borehole soil, wherein at least the portion of said fluid cell comprising said porous medium is covered with a permeable and deformable medium, and wherein said vadose probe comprises an external pressure source connected to one of said one or more conduits for applying pressure/vacuum conditions in said fluid cell.

2. The vadose zone probe according to claim 1, wherein the ends of the elongated body of said vadose zone probe are configured in an acute angle to the front side.

3. The vadose zone probe according to claim 1, wherein the outer surface of the porous medium is curved about its length, and wherein said porous medium is being attached over, or in, an opening formed in a wall of the fluid cell facing the front side of the vadose zone probe such that the outer surface of said porous medium aligns with, or slightly protrudes from, the surface of the front side of said vadose zone probe.

4. The vadose zone probe according to claim 1, wherein the porous medium is an elongated cup having a cavity and an opening being attached over, or in, a corresponding opening provided in the base of the fluid cell.

5. The vadose zone probe according to claim 1, wherein the permeable and deformable medium is implemented by a net, used for enclosing at least a portion of said fluid cell comprising said porous medium, and a grainy material filling the space between said net and said portion of said fluid cell.

6. The vadose zone probe according to claim 1, wherein the permeable and deformable medium is made of a material selected from the group consisting of: porous plastics, sponges, clay, or very soft porous polymer.

7. The vadose zone probe according to claim 1, wherein the porous medium is a porous tip being attached over, or in, a corresponding opening provided in the base of the fluid cell.

8. The vadose zone probe according to claim 1, wherein the vadose zone probe is made from an elongated body having front and rear sides.

9. The vadose zone probe according to claim 8, wherein said rear side is substantially flat and said front side is made from a deformable and permeable material, or having a curvature corresponding to the curvature of said borehole.

10. The vadose zone probe according to claim 1, further comprising one or more sensing means installed in the fluid cell and electrically linked to external monitoring device(s) by means of conducting lines passing along the flexible sleeve.

11. The vadose zone probe according to claim 1, further comprising controllable valves installed on the one or more conduits.

12. The vadose zone probe according to claims 10 or 11, wherein the pressure source, sensing means, and/or controllable valves, are linked to an external control device adapted to receive inputs from said sensors and provide control signals to said pressure source and/or controllable valves.

13. A method for determining the quality and/or purity of soil and pore-water in the vadose zone, comprising:
    drilling a borehole across a section of the vadose zone;
    lowering into said borehole an inflatable sleeve comprising one or more vadose zone probes mounted thereon, said inflatable sleeve adapted to be installed in a borehole formed in the vadose zone, and each of said vadose zone probes comprises a fluid cell having one or more conduits connected thereto for externally accessing its interior, and a porous medium installed in, or formed on, one of its walls for allowing passage of liquid between the interior of said fluid cell and the borehole soil;
    filling said inflatable sleeve with a filling material such that a continuous pressure is applied over said one or more vadose zone probes, thereby pressing them against the wall of the borehole and obtaining hydraulic continuity therebetween through said porous medium;
    introducing a volume of liquid into said fluid cells via said one or more conduits; and whenever needed, removing volumes of liquid from said fluid cell via said one or more conduits.

14. The method according to claim 13, further comprising measuring the pressure in the fluid cells by means of pressure sensing means installed in said fluid cells, wherein said measuring is carried via conducting wires electrically connected thereto.

15. The method according to claim 13, further comprising controlling the level of liquid contained in the fluid cells by means of liquid level sensing means installed thereinside such that whenever the level of liquid in a fluid cell exceeds a predetermined upper threshold a volume of liquid is removed therefrom via said one or more conduits, and whenever the level of liquid in a fluid cell is beyond a predetermined lower threshold level a volume of liquid is introduced thereto via said one or more conduits.

16. The method according to claim 15, further comprising applying pressure/vacuum conditions in the fluid cell via the one or more conduits whenever removing/introducing a volume of liquid from the fluid cell.

17. The method according to any one of claims 13 to 16 further comprising controlling the passage of fluids through the one or more conduits by means of controllable valves installed thereon.

18. A system for determining the quality and/or purity of soil and pore-water in the vadose zone, comprising:
    an inflatable sleeve adapted to be installed in a borehole formed in the vadose zone; and
    one or more vadose zone probes mounted on said inflatable sleeve, said vadose zone probes comprises a fluid cell having one or more conduits connected thereto for externally accessing its interior, and a porous medium installed in, or formed on, one of its walls for allowing passage of liquid between the interior of said fluid cell and the borehole soil, wherein said porous medium being attached over, or in, a corresponding opening provided in the base of said fluid cell, and wherein at least the portion of said fluid cell comprising said porous medium is covered with a permeable and deformable medium, and wherein said one or more vadose zone probes comprises an external pressure source connected to one of said one or more conduits for applying pressure/vacuum conditions in said one or more vadose zone probes fluid cell.

19. The system according to claim 18, wherein the inflatable sleeve is inflated with filling material selected from the following group of material: dry sand, gas, liquid, solidifying liquid, two-component urethane, concrete, epoxy resin, and foaming material.

20. A vadose zone probe adapted to be mounted on an inflatable sleeve for installation in a borehole formed in the vadose zone, comprising: a fluid cell having one or more conduits connected thereto for externally accessing its interior, and a porous medium installed in, or formed on, one of its walls for allowing passage of liquid between the interior of said fluid cell and the borehole soil, wherein at least the portion of said fluid cell comprising said porous medium is covered with a permeable and deformable medium, and wherein said vadose probe comprises one or more sensing means installed in the fluid cell and electrically linked to at least one external monitoring device by means of conducting lines passing along the flexible sleeve.

21. A vadose zone probe according to claim 20 wherein the sensing means, are linked to an external control device adapted to receive inputs from said sensing means.

22. A vadose zone probe adapted to be mounted on an inflatable sleeve for installation in a borehole formed in the vadose zone, comprising: a fluid cell having one or more conduits connected thereto for externally accessing its interior, and a porous medium installed in, or formed on, one of its walls for allowing passage of liquid between the interior of said fluid cell and the borehole soil, wherein at least the portion of said fluid cell comprising said porous medium is covered with a permeable and deformable medium, and wherein said vadose probe comprises controllable valves installed on the one or more conduits.

23. A vadose zone probe according to claim 22, wherein the controllable valves, are linked to an external control device adapted to provide control signals to said controllable valves.

* * * * *